US00PP34238P2

(12) United States Plant Patent
Bradford et al.

(10) Patent No.: US PP34,238 P2
(45) Date of Patent: May 17, 2022

(54) NECTARINE TREE NAMED 'CANDYSWEET XIII'

(50) Latin Name: *Prunus persica*
Varietal Denomination: Candysweet XIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,909

(22) Filed: Dec. 17, 2021

(51) Int. Cl.
*A01H 5/08* (2018.01)
*A01H 6/74* (2018.01)

(52) U.S. Cl.
USPC ..... Plt./190

(58) Field of Classification Search
USPC ..... Plt./187, 190
See application file for complete search history.

(56) References Cited

U.S. PATENT DOCUMENTS

PP16,494 P2 5/2006 Bradford
PP21,927 P2 5/2011 Bradford

*Primary Examiner* — Susan McCormick Ewoldt

(57) ABSTRACT

The present invention relates to a new and distinct variety of nectarine tree, *Prunus persica*, broadly characterized by a medium size, moderately vigorous, hardy, self-fertile, productive and regular bearing tree. The variety has a small non-showy blossom and blooms during the late season, with a chilling requirement of about 650 hours. The fruit matures under the ecological conditions described in mid July, with first picking on Jul. 9, 2021. The fruit is uniform, large in size, sub-acidic and sweet in flavor, globose in shape, clingstone in type, firm in texture, yellow in flesh color, dark red with only light freckling in skin color, and has a bitter tasting kernel.

1 Drawing Sheet

Botanical classification: *Prunus persica.*
Variety denomination: 'CANDYSWEET XIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Candysweet XIII'.

The present variety was hybridized by us in 2013 as a first generation cross using 'Giant Bright' (U.S. Plant Pat. No. 21,927) nectarine as the selected seed parent and '26P994' (unpatented) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2017 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Giant Bright' (U.S. Plant Pat. No. 21,927) nectarine by having a medium size tree, being moderately vigorous, by being self-fertile, by having a small blossom, by blooming in the late season, and by producing nectarines that are mostly red in skin color, that are yellow in flesh color, and that are clingstone in type, but is quite distinguished from it by producing fruit that is sub-acidic instead of acidic in flavor, that is sweeter, that is larger in size, that has a bitter instead of sweet kernel, and that ripens about eight days earlier.

The present variety is similar to its pollen parent, '26P994' (unpatented) nectarine, by being self-fertile and by producing nectarines that ripen in mid July and that are yellow in flesh color and clingstone in type, but is quite distinguished from it by having a small instead of large flower, by producing nectarines that are much sweeter in flavor, much darker red in skin color, and much firmer in texture.

The present variety is most similar to 'Grand Bright' (U.S. Plant Pat. No. 16,494) nectarine by having reniform leaf glands, by being self-fertile, by having a similar chilling requirement, and by producing nectarines that are mostly red in skin color, yellow in flesh color, clingstone in type, firm in texture, and fairly globose in shape, but is distinguished therefrom by producing nectarines that are larger in size, that are sub-acidic instead of acidic in flavor, that are much sweeter, that have a bitter instead of sweet kernel, and that mature four days earlier.

SUMMARY OF VARIETY

In summary, the present nectarine variety is characterized by a medium size, moderately vigorous, hardy, self-fertile, productive and regular bearing tree. The variety has a small non-showy blossom and blooms during the late season, with a chilling requirement of about 650 hours. The fruit matures under the ecological conditions described in mid July, with first picking on Jul. 9, 2021. The fruit is uniform, large in size, sub-acidic and sweet in flavor, globose in shape, clingstone in type, firm in texture, yellow in flesh color, dark red with only light freckling in skin color, and has a bitter tasting kernel.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 15, 2021, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: 'Giant Bright' (U.S. Plant Pat. No. 21,927) nectarine.
Pollen parent: '26P994' (unpatented) nectarine.

TREE

Size: Medium, reaching and maintaining a height of 9' [2.74 m.] and a spread of 9' [2.74 m.] after eight growing seasons utilizing typical dormant pruning.
Vigor: Moderately vigorous, responding about average to irrigation and fertilization. The variety grows about 2' [0.61 m.] of surplus top-growth during the spring and summer. The plant should be grown on a standard commercial rootstock for production purposes.
Growth: Spreading and dense.
Form: Pruned to a vase shape.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Chilling requirement: About 650 hours.
Leaf bud burst: Medium, during the middle of flowering.
Trunk:
- *Size*.—Medium, reaching a maximum diameter of 5½" [139.7 mm.] after the eighth growing season.
- *Texture*.—Shaggy.
- *Bark color*.—A Light grayish brown [60. l.gy.Br] and Brownish gray [64. brGy] variegation with Dark grayish brown [62. d.gy.Br] crevices present.
- *Lenticels*.—Approximate Number Per Square Inch: 12. Color: Strong yellowish brown [74. s.yBr]. Average Size: ⅜" [9.5 mm.] in length. The width is typically one fourth as much as the length. Shape: Elongated.

Branches:
- *Size*.—Medium, diameter of main scaffold is 2½" [63.5 mm.] measured 12" above the crotch, diameter of limb is 1½" [38.1 mm.] measured 12" above the first fork.
- *Texture*.—Smooth to medium on first and second year wood, increasing in roughness with age.
- *Color*.—1st Year Wood Topside: Grayish red [19. gy.R]. 1st Year Wood Underside: Brilliant yellow green [116. brill.YG]. Older Wood: A Grayish yellowish brown [80. gy.yBr] and Moderate yellowish brown [77. m.yBr] variegation with Deep yellowish brown [75. deep yBr] crevices present.
- *Lenticels*.—Number Per Square Inch: About 30 on second year wood. Color: Deep orange yellow [69. deep OY]. Average Size: Small, 1/16" [1.6 mm.] in length. The width is typically one fourth as much as the length. Shape: Elongated.

Leaves:
- *Size*.—Medium to large. Average Length: 5½" [139.7 mm.]. Average Width: 1 13/16" [46.0 mm.].
- *Arrangement*.—Alternate.
- *Thickness*.—Medium.
- *Form*.—Elliptical.
- *Apex*.—Acuminate.
- *Base*.—Rounded to acute, with an average base angle of seventy-five degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: ½" [12.7 mm.]. Average Thickness: 1/16" [1.6 mm.]. Color: Moderate greenish yellow [102. m.gY].
- *Stipules*.—Number: 2 per leaf, up to 6 per growing tip. Average Length: ¼" [6.4 mm.]. Color: Brilliant yellow green [116. brill.YG] becoming Grayish red [19. gy.R] with age.
- *Glands*.—Number: 2 to 4 per leaf. Position: Mostly alternate, first pair is located at the intersection of petiole and base of blade. Form: Reniform. Size: Medium, about 1/32" [0.8 mm.] in length, about 1/64" [0.4 mm.] in width. Color: Brilliant yellow green [116. brill.YG] becoming Dark brown [59. d.Br] with age.
- *Leaf buds*.—Pointed.

Flower buds:
- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.

*Tip color*.—Strong purplish pink [247. s.pPk] with anthers and stigma usually protruding.

Flowers: Perfect, complete, perigynous, usually a single pistil, about thirty stamens, five sepal and petal locations alternately positioned.

*Type*.—Non-showy, small.

*Average flower diameter*.—1 5/16" [33.3 mm.].

*Average flower depth*.—5/16" [7.9 mm.] when fully open.

*Average pedicel length*.—1/8" [3.2 mm.].

*Number of petals*.—Mostly five, extra petal fragments very common, double blossoms occasionally observed.

*Petal arrangement*.—Non-overlapping.

*Petal shape*.—Oval to somewhat obovate.

*Petal margin*.—Entire, very wavy.

*Average petal diameter*.—3/8" [9.5 mm.].

*Average petal length*.—9/16" [14.3 mm.].

*Petal apex*.—Rounded.

*Petal base*.—Rounded.

*Petal color*.—Deep purplish pink [248. deep pPk] toward the apex, Light pink [4. l.Pink] toward the base on both sides.

*Anther color*.—Moderate pink [5. m.Pink] surrounding a Brilliant yellow [83. brill.Y] center at bloom onset.

*Pollen*.—Anthers produce a moderate amount of Brilliant yellow [83. brill.Y] pollen.

*Stigma color*.—Light greenish yellow [101. l.gY].

*Stigma position*.—Typically located about 1/8" [3.2 mm.] above nearby anthers.

*Stamen position*.—Typically located about 1/16" [1.6 mm.] below the petals.

*Average pistil length*.—3/4" [19.1 mm.].

*Average stamen length*.—7/16" [11.1 mm.].

*Ovary*.—Non-pubescent.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—1/4" [6.4 mm.].

*Sepal width*.—3/16" [4.8 mm.].

*Sepal apex*.—Rounded to elliptical to match the sepal length and width.

*Sepal margin*.—Fairly smooth.

*Sepal outer surface*.—Pubescent.

*Fragrance*.—Moderate.

*Blooming period*.—Late compared to other varieties, blooms at the same time as 'Autumn Bright' (U.S. Plant Pat. No. 18,751) nectarine.

*Onset of bloom*.—One percent on Feb. 26, 2021.

*Date of full bloom*.—Mar. 8, 2021.

*Duration of bloom*.—One to two weeks, dependent on ambient temperature.

*Bloom density*.—Moderate.

*Number per cluster*.—1 to 3 with single flowers most common.

FRUIT

Maturity when described: Firm ripe, Jul. 15, 2021.

Date of first picking: Jul. 9, 2021.

Date of last picking: Jul. 22, 2021.

Size: Uniform, large.

*Average diameter axially*.—3 1/4" [82.6 mm.].

*Average diameter across suture plane*.—3 1/4" [82.6 mm.].

*Average diameter across cheek plane*.—3 3/16" [81.0 mm.].

*Typical weight*.—11.0 ounces [312 grams].

Form: Uniform, fairly globose, mostly symmetrical.

*Longitudinal section form*.—Round.

*Axial view*.—Round.

Suture: Extends from the stem cavity, along the side, and ends with a slight depression just beyond pistil point.

*Near the base*.—A sharp groove.

*Along the side*.—A shallow trough.

*Near the apex*.—A medium groove.

Ventral surface: Rounded, lipped on both sides.

Lips: Mostly equal, occasionally unequal.

Cavity: Flaring with Strong orange yellow [68. s.OY] stem markings present.

*Depth*.—5/8" [15.9 mm.].

*Breadth*.—1 5/16" [33.3 mm.].

Base: Truncate.

Apex: Rounded, cordate if viewed parallel to the suture.

Pistil point: Oblique, depressed within the suture, about 1/16" [1.6 mm.] in length.

Stem: Medium.

*Average length*.—3/8" [9.5 mm.].

*Average width*.—3/16" [4.8 mm.].

Skin:

*Thickness*.—Medium.

*Surface*.—Smooth.

*Tenacity*.—Tenacious to the flesh.

*Astringency*.—Non-astringent.

*Tendency to crack*.—Very slight.

*Color*.—Dark red [16. d.R] over a Deep reddish orange [36. deep rO] background with a small amount of Light orange yellow [70. l.OY] freckling toward the apex.

Flesh:

*Color*.—Vivid orange yellow [66. v.OY] with a slight amount of Strong red [12. s.R] bleeding toward the stone.

*Surface of pit cavity*.—Covered with Vivid orange yellow [66. v.OY] broken fibers when twisted away from the stone.

*Amygdalin*.—Scarce.

*Juice*.—Moderate.

*Texture*.—Firm, crisp.

*Fibers*.—Abundant, tender.

*Ripens*.—Fairly even, slightly earlier toward the apex.

*Flavor*.—Sub-acidic, sweet, typically 18 brix.

*Aroma*.—Moderate.

*Eating quality*.—Excellent.

STONE

Type: Clingstone.

Form: Oval.

Hilum: Narrow, oval.

Base: Rounded to slightly truncate.

Apex: Acute.

Sides: Equal.

Tip: Sharp, typically 1/16" [1.6 mm.] in length.

Surface: Irregularly furrowed toward the apex, pitted toward the base.

Ridges: Jagged.

External color: Strong reddish brown [40. s.rBr] when first removed.
Pit wall color when cracked: Deep yellowish brown [75. deep yBr].
Cavity surface color: Strong yellowish brown [74. s.yBr].
Average pit wall thickness: 3/16" [4.8 mm.].
Average length: 1 5/8" [41.3 mm.].
Average width: 1 1/16" [27.0 mm.].
Average breadth: 3/4" [19.1 mm.].
Tendency to split: None observed.
Kernel:
*Form*.—Oval.
*Skin color*.—Light yellow [86. l.Y].
*Pellicle color*.—Moderate olive brown [95. m.OlBr].
*Vein color*.—Strong yellow [84. s.Y].
*Taste*.—Bitter.
*Viable*.—Yes.
*Average length*.—13/16" [20.6 mm.].
*Average width*.—9/16" [14.3 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Grand Bright' (U.S. Plant Pat. No. 16,494) nectarine by having reniform leaf glands, by being self-fertile, by having a similar chilling requirement, and by producing nectarines that are mostly red in skin color, yellow in flesh color, clingstone in type, firm in texture, and fairly globose in shape, but is distinguished therefrom by producing nectarines that are larger in size, that are sub-acidic instead of acidic in flavor, that are much sweeter, that have a bitter instead of sweet kernel, and that mature four days earlier.

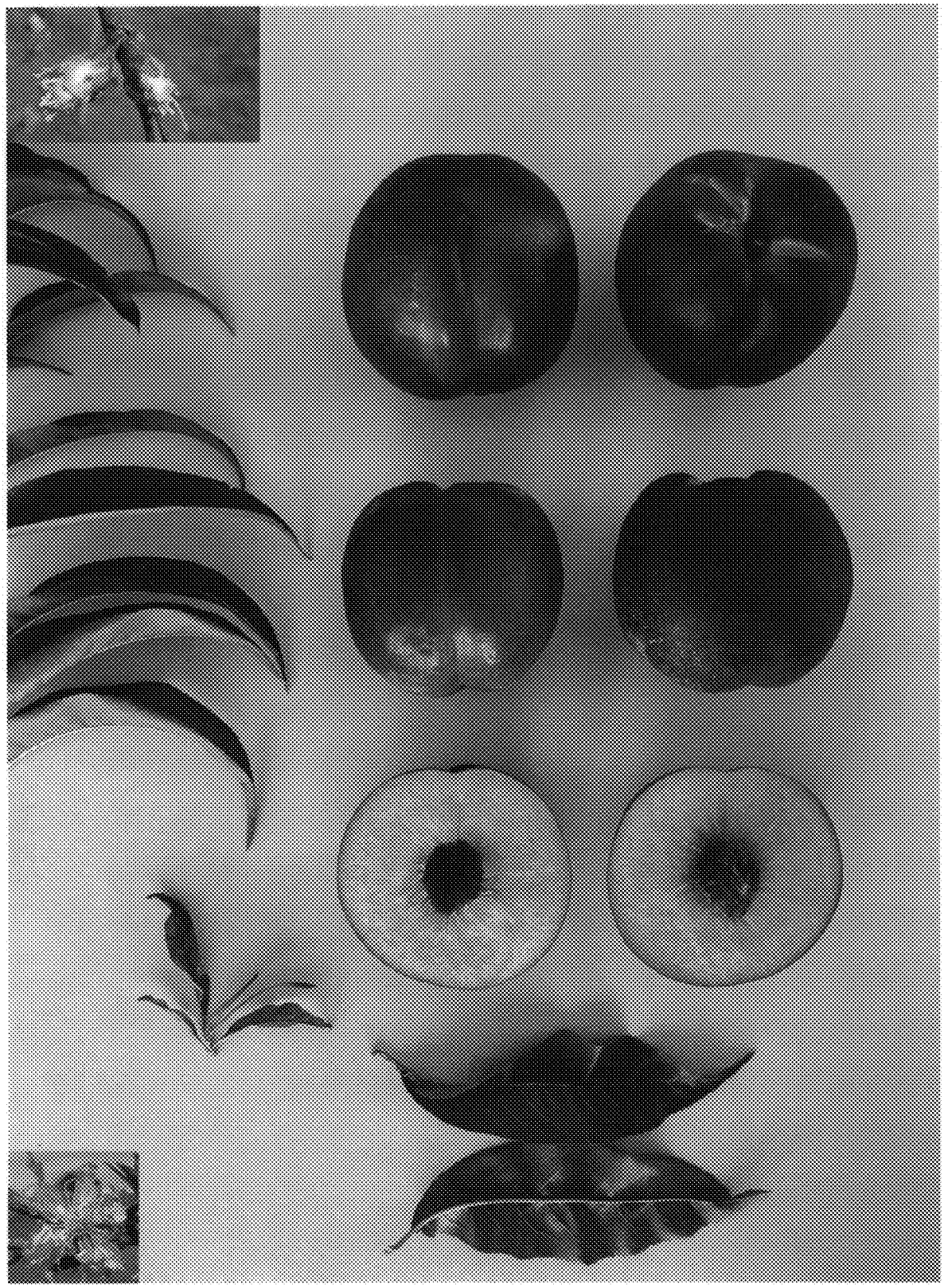

* * * * *